US006784211B1

(12) United States Patent
McPartland

(10) Patent No.: US 6,784,211 B1
(45) Date of Patent: Aug. 31, 2004

(54) ANT SPRAY CONTAINING D-LIMONENE AND METHODS OF MAKING AND USING THE SAME

(76) Inventor: Tor McPartland, 7 Trampa Canyon Rd., Carmel Valley, CA (US) 93924

( * ) Notice: Subject to any disclaimer, the term of this patent is extended or adjusted under 35 U.S.C. 154(b) by 204 days.

(21) Appl. No.: 09/706,158

(22) Filed: Nov. 3, 2000

Related U.S. Application Data

(63) Continuation-in-part of application No. 09/218,732, filed on Dec. 22, 1998, now abandoned, which is a continuation-in-part of application No. 08/846,351, filed on Apr. 30, 1997, now abandoned.

(51) Int. Cl.⁷ ............................................. A61K 31/015
(52) U.S. Cl. ..................................................... 514/763
(58) Field of Search ........................................ 514/763

(56) References Cited

U.S. PATENT DOCUMENTS

| | | | |
|---|---|---|---|
| 3,023,144 A | | 2/1962 | Greathouse |
| 3,930,010 A | * | 12/1975 | Klopping ..................... 424/22 |
| 4,379,168 A | * | 4/1983 | Dotolo ........................ 424/356 |
| 4,616,036 A | | 10/1986 | Hodgin ........................ 514/470 |
| 4,933,371 A | | 6/1990 | Hink et al. .................. 514/739 |
| 5,085,849 A | | 2/1992 | Sampson et al. ............. 424/45 |
| 5,118,506 A | | 6/1992 | Eichofer .................. 424/196.1 |
| 5,194,264 A | * | 3/1993 | Van Tonder ................ 424/405 |
| 5,474,712 A | | 12/1995 | Dotolo et al. ................ 252/550 |
| 5,509,940 A | * | 4/1996 | Zbar et al. ...................... 8/617 |
| 5,653,991 A | | 8/1997 | Rod ............................. 424/406 |
| 5,951,992 A | * | 9/1999 | Wilkins, Jr. .................. 424/405 |
| 6,063,771 A | * | 5/2000 | Snyder ........................ 514/31 |

FOREIGN PATENT DOCUMENTS

| | | | |
|---|---|---|---|
| CA | 2060594 | * | 8/1992 |
| GB | 1603047 | | 11/1981 |

OTHER PUBLICATIONS

R. N. Sharma and K. N. Saxena, "Orientation and Developmental Inhibition in the Housefly by Certain Terpenoids", J. Med. Ent., Nov. 25, 1974, pp. 617–621.

K.A. Powers et al., ". . . Toxicity of an Insecticidal Spray Containing Linalool, D–Limonene, and Piperonyl Butoxide Applied Topically to Domestic Cats", Vet Hum Toxicol 30, Jun. 1988, pp. 206–210.

* cited by examiner

Primary Examiner—Alton N. Pryor
(74) Attorney, Agent, or Firm—Jeffer, Mangels, Butler & Marmaro LLP

(57) ABSTRACT

A food-grade insecticidal composition effective in controlling insects, such as ants, aphids, mealy bugs, white flies, spider mites, leaf hoppers, cabbage loopers, leaf eating beetles and caterpillars, cockroaches, flies, wasps, body and head lice but which is non-toxic to humans and household animals includes an effective insect-controlling amount of D-limonene, a non-toxic emulsifying agent, and a non-toxic hydrophilic solvent.

1 Claim, No Drawings

ANT SPRAY CONTAINING D-LIMONENE AND METHODS OF MAKING AND USING THE SAME

This is a continuation-in-part of U.S. patent application Ser. No. 09/218,732, filed Dec. 22, 1998, which is a continuation-in-part of U.S. patent application Ser. No. 08/846,351, filed Apr. 30, 1997, both of which are now abandoned and the disclosures of which are incorporated in their entirety herein by reference.

FIELD OF THE INVENTION

The present invention relates to an all-natural, food grade insecticidal composition that is effective in controlling insects including ants, aphids, mealy bugs, white flies, spider mites, leaf hoppers, cabbage loopers, leaf eating beetles and caterpillars, cockroaches, flies, wasps, body and head lice and more particularly relates to an insecticidal composition that contains D-limonene, a non-toxic hydrophilic solvent, a non-toxic emulsifying agent, and a preservative, that is an effective residual repellant and contact insecticide but is non-toxic to humans and household animals, and not harmful to landscaping, particularly rose bushes and ornamentals, indoor plants or the environment.

BACKGROUND OF THE INVENTION

Numerous pesticide and insecticide products are available in the market for killing insects such as ants. However, these products are generally toxic to humans and household animals, and harmful to plants and the environment. Therefore they must be administered with extreme care. This is especially a problem in the termination of ants, cockroaches and the like because they normally appear near food where a careless use of insecticides may cause accidental poisoning of humans and household animals.

Other insecticide products containing D-Limonene disperse the D-Limonene in mineral oil petroleum distillates which may be harmful if accidentally ingested and may cause damage to plants. Unlike the compositions of the present invention, no emulsifier is used because the D-Limonene is dispersed in oil and not water.

Lice infestation of humans, particularly children, is still treated with compositions that contain the pesticide lindane. Lindane is carcinogenic and an estrogen mimic. There exists a need for a composition which can treat body and head lice but which is safe to use, particularly on children.

U.S. Pat. No. 4,379,168 to Dotolo discloses pesticides containing D-limonene as an insect-killing ingredient along with water-soluble surfactants or emulsifiers, and water. The pesticide compositions are designed for use mainly as a dip to rid small animals of fleas and ticks and as a spray to kill fleas and ticks on small animals. None of the compositions taught by Dotolo contain suitable amounts of emulsifying agent and D-limonene for the purpose of the present invention. None of the compositions taught by Dotolo contain any surfactants or emulsifiers that were selected for their safety. For example, the Kodak Laboratory Chemical Catalog No. 51 indicates that Triton X-100, which is disclosed as an acceptable emulsifier in Dotolo, is irritating to the skin and eyes.

U.S. Pat. No. 3,023,144 to Greathouse, et al. discloses germicides and fungicides containing about 25% by weight D-limonene, about 1% by weight of p-methyl acetophenone, and other unsaturated hydrocarbon cleavage products of D-limonene, up to about 7% by weight concentrated citrus oil foots and from 0.25% up to about 10% by weight salicylic acid. The compositions are used for topical application on humans and animals to control infections of skin and external organs arising from wounds or from infestation by fungi, bacteria, and larvae. Greathouse discloses that the active ingredient for the biocidal activity of the compositions disclosed is not D-limonene but rather compounds such as p-methyl acetophenone, and other unsaturated hydrocarbon cleavage products of D-limonene.

A need exists for an insecticidal composition that kills on contact and controls insects such as ants, aphids, mealy bugs, white flies, spider mites, leaf hoppers, cabbage loopers, leaf eating beetles and caterpillars, cockroaches, flies, wasps, body and head lice by repelling them, and which is non-toxic to humans, household animals and house plants.

A need also exists for an insecticidal composition that is effective in controlling insects such as ants, aphids, mealy bugs, white flies, spider mites, leaf hoppers, cabbage loopers, leaf eating beetles and caterpillars, spiders, earwigs, slugs and snails, cockroaches, flies, wasps, body and head lice by killing them, and which is non-toxic to humans, household animals and house plants.

There is also a need for a safe and effective treatment for lice infestation of a human.

A need also exists for an insecticidal composition that contains an insecticide made from a natural substance that is part of and therefore not harmful to landscaping, particularly rose bushes and ornamentals, indoor plants or the environment.

A need also exists for an insecticidal composition that can be used around food, humans and pets without worry.

SUMMARY OF THE PREFERRED EMBODIMENTS

In accordance with one aspect of the present invention, there is provided a food-grade insecticidal composition that includes an amount of D-limonene sufficient to provide insect control, a non-toxic hydrophilic solvent, and an amount of a non-toxic emulsifying agent sufficient to solubilize D-limonene in the solvent.

Preferably, the inventive composition includes about 1% to about 20% by weight of D-limonene, about 1% to about 25% by weight of the selected non-toxic emulsifying agent, for example Alkamuls EL620, and about 98% to about 55% by weight of the selected non-toxic hydrophilic solvent.

In a preferred embodiment, the inventive composition also includes at least one food-grade preservative, such as sodium benzoate.

Methods of making and using the inventive compositions are also provided.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The non-toxic insecticidal compositions according to the present invention have a pleasant citrus scent and are suitable for use in any living environment. In particular, the inventive compositions are made only from food-grade ingredients. As used herein, an ingredient or a composition is "food-grade" if it meets the U.S.F.D.A.'s G.R.A.S. (Generally Recognized as Safe) food grade standard. Additionally, in a preferred embodiment of the invention, the inventive compositions are made only from organic ingredients. As used herein, an ingredient or a composition is "organic" if it is made mainly of naturally occuring materials. Thus, the inventive compositions are not only safe and non-toxic to humans and household animals such as dogs, cats, rabbits, birds, lizards, etc., but can also be used near food without any danger of contamination or accidental poisoning, and are safe even if ingested by humans or household animals. The inventive compositions will not harm landscaping foliage or indoor plants. Since the inventive compositions are made of mainly naturally occurring materials, they are not harmful to the environment and do not cause any unwanted pollution. They are also completely biodegradable.

D-limonene, otherwise known as orange limonene or 1-methyl-4-(1-methylethenyl) cyclohexene or 4-isopropenyl-1-methyl cyclohexene, has a chemical formula of $C_{10}H_{16}$, a molecular weight of 136.2, and contains 88.1% C and 11.8% H by weight. It occurs in various ethereal oils, particularly in oils of lemon, orange, lime, grapefruit and bergamot. D-limonene can be obtained from steam extraction of citrus peels of orange, lemon, lime, grapefruit and bergamot, some of the extractions can contain as high as 90% D-limonene. The invention thus provides a valuable use for what would otherwise be a waste product. Distillation of the oils produces technical grades of D-limonene of higher purity, i.e., from about 95% to about 96%. D-limonene has a pleasant citrus scent. It can be suitably used in any living environment.

The D-form of limonene is a liquid having a boiling point of 175.5–176 degrees. centigrade. It can be commercially obtained from Lykes Pasco Packing Company (Dade City, Fla.) or Florida Chemical Company (Lake Alfred, Fla.).

The compositions of the present invention allow a user to provide insect control in interior and exterior settings. Insect control can include repelling and/or killing insects, such that less insects are alive or present in a given area than if the compositions of the present invention had not been applied in the area. The inventive compositions control a wide range of insects, including without limitations ants, aphids, mealy bugs, white flies, spider mites, leaf hoppers, cabbage loopers, leaf eating beetles and caterpillars, cockroaches, flies, wasps, body lice and head lice.

While not limiting the invention by any particular theory, it is believed that the D-limonene acts to soften the waxy coating on the exoskeleton of insects and thereby causes the softened coating to clog the external insect respiratory organs, known as spiracles. The clogged spiracles interfere with the ability of the insect to obtain adequate amounts of oxygen, ultimately resulting in the death of the insect. This invention is therefore also suitable against other pests, besides insects, which would be susceptible to the external effects set forth above.

The inventive compositions include-a food-grade, non-toxic hydrophilic solvent. Water is particularly preferred as the solvent. Other non-toxic hydrophilic solvents, for example, ethanol, dilute acetic acid solutions, and the like can also be used.

Useful emulsifying agents include polyethoxylated castor oils. One such emulsifying agent is available commercially under the trade name of Alkamuls EL620 from Rhone Poulenc Co. It is non-toxic to humans, household animals and house plants and landscaping and will not cause skin or eye irritation. Castor oils also improve the insecticidal effect of the formulation. Other commercially available emulsifying agents that are non-toxic, such as polyoxyethylenesorbitans supplied by ICI Americas or Sigma Chemical Company, may also be suitably used for the present invention provided that they are food-grade. In a preferred embodiment a polyoxyethylenesorbitan monooleate such as Tween 80 may be used.

In general, the emulsifying agent should be present in an amount sufficient to render the D-limonene soluble in the non-toxic hydrophilic solvent. When a polyethoxylated castor oil is used, it should contain sufficient polyethoxylation to render the D-limonene soluble in a non-toxic hydrophilic solvent when the emulsifying agent is used in an amount as disclosed herein. When that solvent is water, the temperature of the water when combined with the other ingredients of the composition should be about 95° F. for optimal emulsification.

In order to provide a reasonable shelf-life to the insecticidal compositions, it is preferable that a preservative be added to the composition. One such suitable preservative is sodium benzoate commercially supplied by Pfizer, Inc. Other commercially available preservatives used for preserving food, as would be known to those of ordinary skill in the art, may also be suitably used.

Preferred embodiments of the inventive insecticidal composition, which are suitable for application as a spray, include about 0.7% to about 20% by weight, more preferably about 0.7% to about 10% by weight, of D-limonene, and even more preferably about 0.775% by weight D-limonene; between about 1% to about 25% by weight, more preferably about 5% to about 15% by weight, of a non-toxic emulsifying agent; about 0.01% to about 5% by weight, more preferably about 0.01% to about 1.0% by weight, of a preservative; and the balance of the selected solvent.

Preferably, the inventive compositions are free of petroleum distillates.

When the novel insecticidal compositions are used indoors as a spray, they should be sprayed preferably from about 6 to about 8 inches away from and directly on insects such as ants, or on insect trails such as ant trails to the source of the insects such as ants (e.g., ant colonies, nests, etc.) and sprayed until visibly wet. Insects are typically killed within minutes of contact with the novel insecticidal compositions.

The insecticidal compositions can be used on the interior surfaces in a building such as counter tops and in food preparation areas. For outdoor use, the insecticidal compositions of the present invention should be applied at the perimeter of a building such as a home, at insect trails such as ant trails, at insect nests, such as ant nests and at doors, cracks, and window frames where insects such as ants may enter the building. It should be applied until visibly wet. It will provide lasting repellent qualities.

Application of the present insecticidal compositions is preferably effected by spraying of the insecticidal compositions by conventional spray apparatus such as aerosol cans bug sprayers and the like. However, application may also be effected by any means of contacting surfaces to be treated, for example, with a brush which has been dipped in the insecticidal compositions. Because the novel insecticidal compositions are non-toxic, they can also be applied with a human hand.

When the present invention is applied to solid surfaces and left to remain there, the residual effect of the insecticidal composition will last for a period of time effectively keeping insects, such as ants, away from the treated area.

The inventive insecticidal compositions can also be applied to a plant, such as a rose bush or other ornamental plant, in order to control insects.

Further embodiments of the inventive compositions can be formulated for use in treating humans, particularly children, infected with lice, particularly head lice. When the novel insecticidal composition is used to treat humans infected with lice, it should be applied to the infected area, such as the scalp and left on for about 5 minutes after which it may be rinsed and preferably shampooed off.

The invention can be made as a concentrate that can be diluted with water. The invention can be used as a paste and be effective in the control of head and body lice.

Non-limiting examples of the inventive insecticidal composition are set forth below.

EXAMPLE 1

For home, office, school, institutional or industrial applications, indoor and outdoor (proven effective against ants, roaches and fleas but is a broad based insecticide and repellent):
6 wt % D-limonene (0.2% impurities in the D-limonene, net active 5.8%)
10 wt % Alkamuls EL620 (polyethoxylated caster oil)
0.1 wt % sodium benzoate
83.9 wt % water.

The insecticidal composition according to the foregoing specific formulation has a white, opalescent color. Its physical state is a liquid at 25° C. and has a citrus-like odor. It has a boiling point between 99–100° C. and a specific gravity of 0.9753 gm/ml. It is soluble in water and has a pH of 6.1. The flash point of the insecticidal composition is greater than 60° C. It has a viscosity of 1.97 centipoise at 37.8° C.

EXAMPLE 2

For agriculture, on food and ornamental crops (proven effective on aphids and spider mites but useful for many other plan pests):
0.775% D-limonene (0.05% impurities in the d-Limonene, net active 0.725%)
2.5% Alkamuls EL 620
0.025% Sodium Benzoate
95.975% Water (UV sterilized and particulate filtered to 5 microns)

EXAMPLE 3

As a liquid concentrate to make the two previous formulations by simply adding the proper ratio of warm 95° F. water:
18% d-Limonene (0.6% impurities in the d-Limonene, net active 17.4%)
30% Alkamuls EL 620
0.3% Sodium Benzoate
51.7% Water (UV sterilized and particulate filtered to 5 microns)

EXAMPLE 4

As a paste for applying to head and body as a treatment for lice (puts lice into a state of morbidity making for easy removal):
0.8% impurities in the d-limonene, net active 23.2%)
40% Alkamuls EL 620
0.1% Sodium Benzoate
35.9% Water (UV sterilized and particulate filtered to 5 microns)

What is claimed is:

1. A method of eradicating fire ants, comprising:
    applying a formulation to an area to be eradicated of fire ants, wherein said formulation consists essentially of about 0.7% to about 1.5% D-limonene; about 1% to about 25% by weight of an emulsifying agents selected from the group consisting of polyoxyethylenesorbitans and polyethoxylated castor oil; about 98% to about 55% by weight of a non-toxic hydrophilic solvent, and about 0.01% to about 5% by weight of a food-grade preservative; and
    allowing said formulation to remain in contact with said area for a suitable period of time to eradicate said fire ants.

* * * * *